United States Patent

Srinivasan

[11] Patent Number: 5,310,536
[45] Date of Patent: May 10, 1994

[54] LIGANDS FOR IMPROVING METAL CHELATE FORMATION KINETICS

[75] Inventor: Ananthachari Srinivasan, St. Charles, Mo.

[73] Assignee: Mallinckrodt Medical, Inc., St. Louis, Mo.

[21] Appl. No.: 832,149

[22] Filed: Feb. 6, 1992

[51] Int. Cl.$^5$ .................. A61K 49/02; A61K 43/00
[52] U.S. Cl. ................... 424/1.65; 534/10; 534/14; 564/153; 564/154; 548/548; 549/472; 549/475; 546/261; 546/264; 546/290; 546/300; 560/147; 560/169; 562/556
[58] Field of Search ............ 424/1.1; 534/10, 11, 534/12, 14; 564/153, 154; 548/548; 549/472, 475; 546/261, 264, 290, 300; 560/147, 169; 562/556; 530/300, 331, 391.5

[56] References Cited

U.S. PATENT DOCUMENTS

| | | | |
|---|---|---|---|
| 4,638,051 | 1/1987 | Burns et al. | 534/14 |
| 5,071,636 | 12/1991 | Yamauchi et al. | 424/1.1 |
| 5,075,099 | 12/1991 | Srinivasan et al. | 424/1.1 |
| 5,095,111 | 3/1992 | Lever et al. | 540/544 |
| 5,136,038 | 8/1992 | Bodor | 546/169 |
| 5,202,451 | 4/1993 | Fritzberg et al. | 564/154 X |

OTHER PUBLICATIONS

Gustavson et al., "Synthesis of a New Class of Tc Chelating Agents: N$_2$S$_2$ Monoaminemonoamide (MAMA) Ligands" *Tetrahedron Letters*, vol. 32, No. 40, pp. 5485-5488, 1991.

Bryson, N, et al., *Inorganic Chemistry*, vol. 29, No. 16, Aug. 1990.

Misra et al., "Synthesis of a Novel Diaminodithiol Ligand for Labelling Proteins and Small Molecules with Technetium-99m", *Tetrahedron Letters*, vol. 30, No. 15, pp. 1885-1888, 1989.

Baidoo et al., "Synthesis of a Diaminedithiol Bifunctional Chelating Agent for Incorporation of Technetium-99m into Biomolecules", *Bioconjugate Chem.*, vol. 1, pp. 132-137, 1990.

Rao et al., "Tc-Complexation of N$_2$S$_2$Monoaminemonoamides", Pre-publication draft.

*Primary Examiner*—Robert L. Stoll
*Assistant Examiner*—John M. Covert
*Attorney, Agent, or Firm*—Brian K. Stierwalt

[57] ABSTRACT

Amide-thiolate ligands having improved metal chelate formation kinetics are disclosed. The ligands include a tertiary amine strategically located to facilitate rapid formation of an amine-amide-thiolate intermediate complex, followed by transfer of the metal to a thermodynamically stable amide-thiolate complex. The amide-thiolate ligands of the present invention may be used for post formed labeling of biological substances for use in the fields of diagnosis and therapy.

8 Claims, No Drawings

LIGANDS FOR IMPROVING METAL CHELATE FORMATION KINETICS

FIELD OF THE INVENTION

This invention relates generally to novel amide-thiolate ligands having improved metal chelate formation kinetics. The amide-thiolate ligands of the present invention may be used for post formed labeling of biological substances useful in the fields of diagnosis and therapy.

BACKGROUND OF THE INVENTION

Scintigraphic imaging and similar radiographic techniques for visualizing tissues in vivo are finding ever-increasing application in biological and medical research and in diagnostic and therapeutic procedures. Generally, scintigraphic procedures involve the preparation of radioactive agents which upon introduction to a biological subject, becomes localized in the specific organ, tissue or skeletal structure of choice. When so localized, traces, plots or scintiphotos depicting the in vivo distribution of radiographic material can be made by various radiation detectors, e.g., traversing scanners and scintillation cameras. The distribution and corresponding relative intensity of the detected radioactive material not only indicates the space occupied by the targeted tissue, but also indicates a presence of receptors, antigens, aberrations, pathological conditions, and the like.

In general, depending on the type of radionuclide and the target organ or tissue of interest, the compositions comprise a radionuclide, a carrier agent designed to target the specific organ or tissue site, various auxiliary agents which affix the radionuclide to the carrier, water or other delivery vehicles suitable for injection into, or aspiration by, the patient, such as physiological buffers, salts, and the like. The carrier agent attaches or complexes the radionuclide to the peptide carrier agent, which results in localizing the radionuclide being deposited in the location where the carrier agent concentrates in the biological subject.

Triamidethiolate and diamidedithiolate ligands have been used successfully for radiolabeling macromolecules. In general, amide-thiolate systems require harsh (75° C.–100° C.) radiolabeling conditions for preparing Tc and Re complexes. Under these conditions, the stability and biological properties of the small and medium bioactive peptides are often degraded.

In order to avoid harsh labeling conditions, pre-formed complexes have been coupled to the protein with some success. See Fritzberg et al., U.S. Pat. Nos. 4,965,392 and 5,037,630 incorporated herein by reference. In the "pre-formed approach," the ligand is complexed with the radionuclide and then conjugated to the bioactive peptide. A major disadvantage of the pre-formed approach is that the end user must perform both the radiolabeling step and the coupling step (attaching the complex to the bioactive peptide). The final product must be purified prior to administration. In the case of small and medium sized peptides, the metal-complex may potentially react with "active sites" of the peptide. Thus, site specific attachment of a ligand to a bioactive molecule is only possible with post formed complexes.

In the conventional "post-formed approach," the ligand is first conjugated to the peptide and the resulting conjugate is labeled with the radioisotope under complex forming conditions. In the present invention, the post-formed approach has the additional advantage of allowing preparation of the conjugated bioactive peptide in kit form. The end users would perform only the radiolabeling step.

It has been found that the presence of free thiol (instead of protected thiol) and/or replacement of an amide with an amine causes labeling of $N_2S_2$ and $N_3S$ ligands to proceed under milder conditions, but at the expense of some complex stability. See Rao et al., "Tc-Complexation of $N_2S_2$ Monoaminemonoamides," *Int. J. Radiat. Part B*, (1991) (in press). In addition, Misra et al., "Synthesis of a Novel Diaminodithiol Ligand for Labeling Proteins and Small Molecules with Technetium-99m," *Tetrahedron Letters*, Vol. 30, No. 15, pp. 1885–88 (1989) and Baidoo et al., "Synthesis of a Diaminedithiol Bifunctional Chelating Agent for Incorporation of Technetium-99m into Biomolecules," *Bioconjugate Chemistry*, Vol. 1, pp. 132–37 (1990), report that diaminedithiol (DADT) ligands label with $^{99m}Tc$ at ambient temperatures.

Gustavson et al., "Synthesis of a New Class of Tc Chelating Agents: $N_2S_2$ Monoaminemonoamide (MAMA) Ligands," *Tetrahedron Letters*, Vol. 32, No. 40, pp. 5485–88 (1991), compares the radiolabeling efficiency of a $N_2S_2$-diamidedithiol (DADS) ligand with a $N_2S_2$-monoamine amide (MAMA) ligand. It was found that substitution of the amide nitrogen in the DADS ligand with an amine nitrogen in the MAMA ligand produced a threefold increase in radiochemical yield when labeling with $^{99m}Tc$ at 37° C. for 30 minutes.

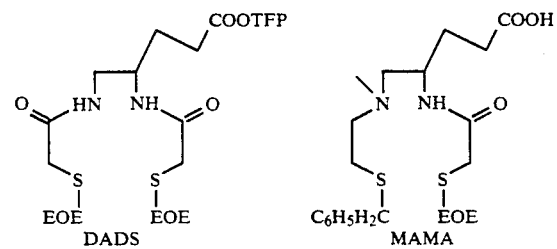

Notwithstanding the improved metal complex formation kinetics reported with amine-containing $N_2S_2$ and $N_3S$ ligands, Tc and Re amide-thiolate complexes assure maximum in vivo stability and inhibit metal oxidation to the pertechnetate or perrhenate oxidation state.

From the foregoing, what is needed in the art is an amide-thiolate ligand with improved complex formation kinetics which can be labeled under mild conditions and which has excellent in vivo complex stability.

SUMMARY OF THE INVENTION

The present invention discloses novel amide-thiolate ligands having improved complex formation kinetics. The present invention also includes radiolabeled peptide compounds utilizing the disclosed ligands, methods of preparing these compounds, pharmaceutical compositions comprising these compounds and the use of these compounds in kits for therapeutic and diagnostic applications.

Conventional amide-thiolate ligands, including $N_3S$ and $N_2S_2$ ligands, are modified according to the present invention to include a center for formation of an amine-amide-thiolate kinetic intermediate complex, followed by transfer of the metal to a thermodynamically stable amide-thiolate core. Amide-thiolate ligands are modified by strategically locating an amine group to facilitate rapid formation of the amine-amide-thiolate intermediate complex. The "amine group" is preferably a tertiary amine, alkylated phosphene, or equivalent group having an unshared pair of electrons capable of being donated to the metal electrophile during complex formation.

In order to form the amine-amide-thiolate intermediate complex, it is important that the amine be at a proper location and distance from the chelating core. For most applications, the amine group is separated from the α carbon of the amino acid by two to five carbons, and preferably by three carbon atoms.

The intermediate complex acts as a built-in metal transfer agent. The amine-amide-thiolate complex formation and transfer of the metal to the amide-thiolate complex occurs under mild conditions. As used herein, the term "mild conditions" includes conditions of complex formation that do not adversely affect the targeting ability or biological activity of the carrier molecule. For most purposes, a complexing temperature in the range from about 25° C. to about 50° C. and a pH in the range from about 3–8 are sufficiently mild for small and medium peptides.

The amide-thiolate ligands within the scope of the present invention can be coupled as conjugates with biologically active molecules or biomolecules that are known to concentrate in the organ or tissues to be examined. These biomolecules include, for example, growth factors such as somatostatin, hormones such as insulin, prostaglandins, steroid hormones, amino sugars, peptides, proteins, lipids etc. Conjugates with albumins, such as human serum albumin, antibodies, monoclonal antibodies specific to tumor associated antigens, or antimyosin etc. The diagnostic media formed therefrom may be used in diagnostic and therapeutic applications.

In the present invention, the amide-thiolate ligand is coupled to the biomolecule according to standard procedures known in the art. In the case of small to medium peptides, the active sites of the biomolecules are protected so that the ligands are specifically attached to functional groups that are not involved in the binding of the biomolecules to the target receptor.

The ligands and biomolecule conjugates described above are useful in diagnostic and radiotherapy applications. The compounds of the present invention may be labeled with any suitable radionuclide favorable for these purposes. Such suitable radionuclides for radiotherapy include but are not limited to $^{186}Re$, $^{188}Re$, $^{67}Cu$, $^{90}Y$, and $^{60}Co$. For diagnostic purposes the most suitable radionuclides include, but are not limited to, the transition metals as exemplified by $^{99m}Tc$, $^{111}In$, and $^{62}Cu$.

It is therefore an object of the present invention to provide an amide-thiolate ligand having improved complex formation kinetics which can be labeled under mild conditions and which has excellent complex stability.

DETAILED DESCRIPTION OF THE INVENTION

The novel amide-thiolate ligands of the present invention are distinguished from conventional amide-thiolate ligands by having an amine group, or its equivalent, on a side chain which participates in the formation of an amine-amide-thiolate intermediate complex. The rapidly formed intermediate complex then transfers the metal to a thermodynamically stable amide-thiolate core. Overall, the metal chelate formation kinetics are enhanced.

The "amine group" is preferably a tertiary amine, alkylated phosphene, or equivalent group having an unshared pair of electrons capable of being donated to the metal electrophile during initial complex formation. Proper location and spacing of the amine group from the chelating core is necessary to form the desired amine-amide-thiolate intermediate complex. The amine group is preferably separated from the α carbon of the amino acid by two to five carbons, and most preferably by three carbon atoms.

The following generalized structures illustrate typical $N_3S$ ligands containing amine groups coupled to side chains which can participate in the formation of intermediate complexes within the scope of the present invention.

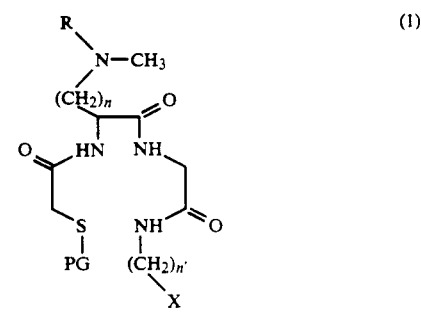

(1)

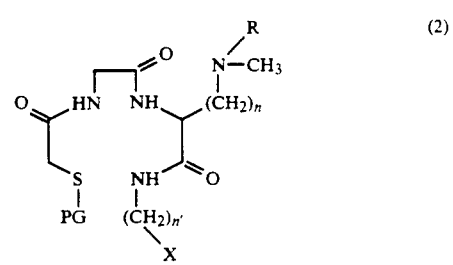

(2)

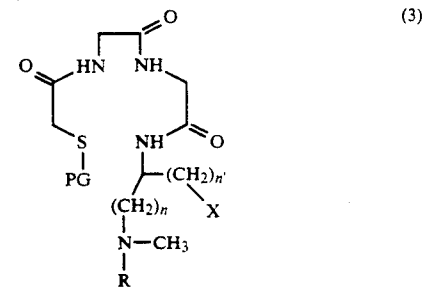

(3)

Where n is in the range from 2–5; n' is in the range from 1–10; X is a functional group capable of reacting with a biomolecule such as a carbonyl, active ester, isocyanate, isothiocyanate, imidate, maleimide or an activated electrophilic center such as C=C, halocarbonyl, halosulfonyl, and haloacetyl; R is methyl or alkyl groups optionally containing functional group X; and PG is a protecting group.

The protecting group prevents potential oxidation of the sulfur and prevents the sulfur from reacting with other reactive groups in the biologically active molecule during attachment of the ligand. The protecting group remains stable during kit formulation and stable until the metal (radioisotope) is added by the end user for conversion to the chelate. The protecting groups are removed concomitantly during complex formation, i.e., the protecting groups are removed only under labeling conditions and in the presence of the metal. Examples of typical protecting groups known in the art include hemithioacetal groups such as ethoxyethyl, methoxymethyl, substituted and unsubstituted tetrahydrofuranyl and tetrahydropyranyl, acetamidoalkyl such as actetamidomethyl, S-acyl such as S-alkanoyl, S-benzoyl, and S-substituted benzoyl groups.

The different side chain lengths can be prepared from modified dimethylamino amino acids; for n=2, from aspartic acid, for n=3, from glutamic acid, for n=3, from ornithine, and n=4, from lysine. The following reactions illustrate how the requisite dialkylamino compounds may be prepared:

For n = 1 and 2

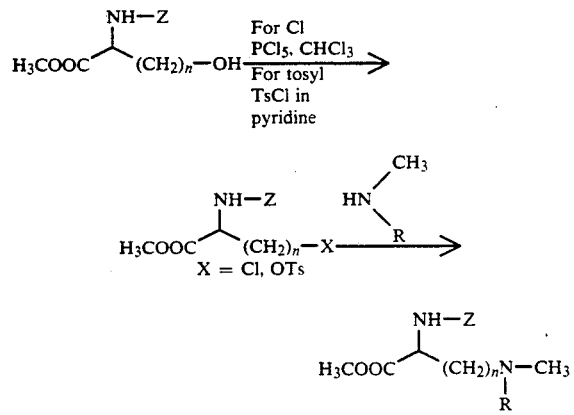

The requisite dialkylamino acid derivatives are prepared from commercially available Z-serine- and Z-threonine methyl ester (Z=benzyloxycarbonyl) derivatives. Dialkylamino groups are introduced by nucleophilic displacement of the Cl or the tosyl derivatives prepared according to the reaction shown below. (For conversion of serine and threonine derivatives to the chloro and tosyl derivatives, see A. Srinivasan, R. W. Stephenson and R. K. Olsen, *J. Org. Chem.*, Vol. 42, p. 2256 (1977)).

For n = 3 and 4

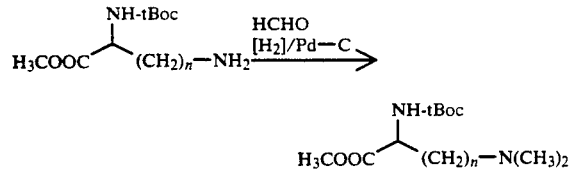

The starting materials are commercially available N-α-tBoc ornithine methyl ester, when n=3, and N-α-tBoc-lysine methyl ester, when n=4. The term "tBoc" is tertiary butoxy carbonyl. This methodology is well known in the art.

For n = 2, 3, and 4

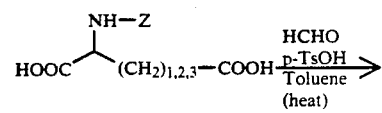

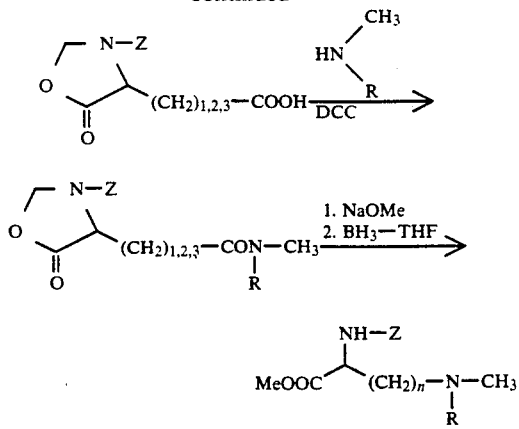

Commercially available N-Z-aspartic- (n=1), N--glutamic-(n=2), and Z-aminoadipic (n=3) are converted to the oxazolidinones in the presence of p-formaldehyde and p-toluenesulfonic acid as the catalyst according to the procedure of R. Straka and M. Zaoral (*Coll. of Czeck. Chem. Comm.*, Vol.42, p. 560 (1977)). The tertiary amide is prepared by DCC mediated condensation of the oxazolidinones (C. Itoh, *Chem. Pharm. Bull.*, Vol. 17, p. 1679 (1969)). After the formation of methyl ester by sodium methoxide, the tertiary amide is reduced to the corresponding amine. (For borane reductions of tertiary amide to amine, see H. C. Brown and P. Heim, *J. Org. Chem.*, Vol. 58, p. 912 (1978)).

For compound (3)

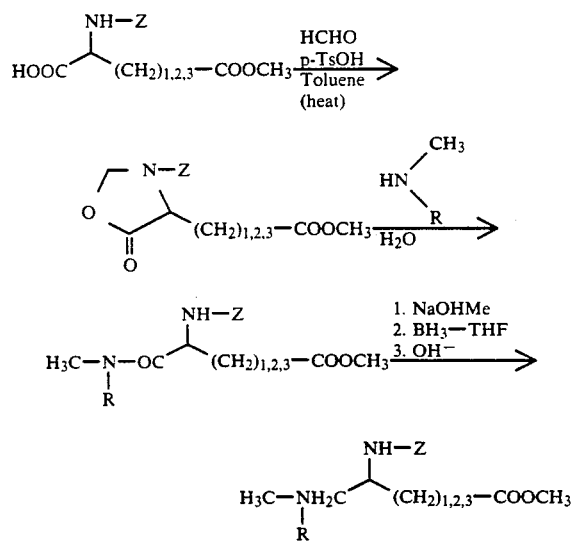

To prepare α-amides, the oxazolidinone distal methyl esters are reacted with requisite amine according to the procedure of K. Lee, et al., *Synthesis.* p. 931 (1991). Reduction of the α-amide to the amine is accomplished by borane reduction. (H. C. Brown and P. Heim, *J. Org. Chem.*, Vol. 58, p. 912 (1978)).

The following generalized structure illustrates one possible $N_2S_2$ ligand containing an amine group coupled to a side chain which can participate in the formation of intermediate complexes within the scope of the present invention.

which converts to a most preferred [5,5,5] triamide-thiolate system.

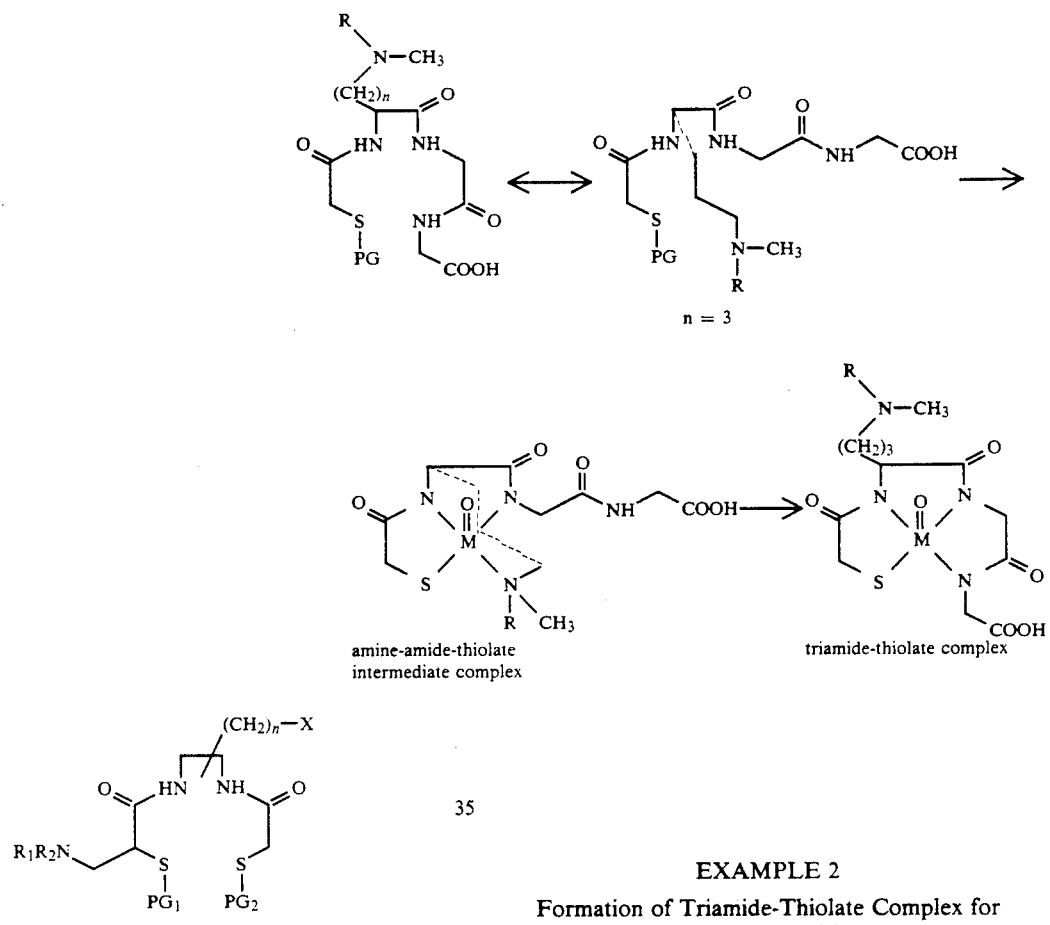

amine-amide-thiolate
intermediate complex triamide-thiolate complex

Where PG$_1$ and PG$_2$ may be the same or different sulfur protecting groups. At least one of PG$_1$ and PG$_2$ should be an acid labile protecting group selected from the group consisting of hemithioacetal groups such as ethoxyethyl and methoxymethyl, substituted and unsubstituted tetrahydrofuranyl and tetrahydropyranyl, acetamidoalkyl such as actetamidomethyl. X is a functional group capable of reacting with a biomolecule such as a carbonyl, active ester, isocyanate, isothiocyanate, imidate, maleimide or an activated electrophilic center such as C=C, halocarbonyl, halosulfonyl, and haloacetyl. R$_1$ and R$_2$ may be the same or different lower alkyl group.

The following examples are offered to further illustrate the formation of triamide-thiolate complexes via an amine-amide-thiolate kinetic intermediate complex within the scope of the present invention. These examples are intended to be purely exemplary and should not be viewed as a limitation on any claimed embodiment.

EXAMPLE 1

Formation of Triamide-Thiolate Complex for Compound (1)

The following diagram illustrates a mechanism for the formation of a triamide-thiolate complex for compound (1) identified above. In the diagram, 3N and S are planar, M=0 forms a tetradentate complex, and n=3. The initial amine-amide-complex is a [5,7,5] system,

EXAMPLE 2

Formation of Triamide-Thiolate Complex for Compound (2)

The following diagram illustrates a mechanism for the formation of a triamide-thiolate complex for compound (2) identified above. In the diagram n=2. The initial amine-amide-complex is a [5,6,5] system, which converts to a most preferred [5,5,5] triamide-thiolate system. The M—N(R)—CH$_3$ is then displaced by the amide to form the triamide-thiolate complex. The more favorable ring size in the intermediate complex makes compound (2) preferable over compound(1).

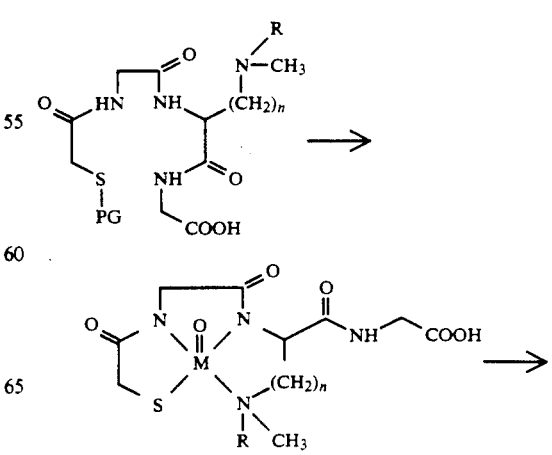

-continued

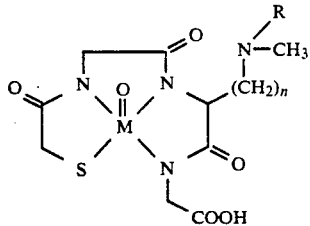

EXAMPLE 3

Formation of Triamide-Thiolate Complex for Compound (3)

The following diagram illustrates a mechanism for the formation of a triamide-thiolate complex for compound (3) identified above having a terminal dialkylaminomethyl amino acid. Unlike compounds (1) and (2), a transannular displacement mechanism in an either membered intermediate complex leads to stale triamide-thiolate complex formation. Compound (3) is based on α-dimethylamino amino acids rather than tertiary amine containing α-amino acids. As described in Example 6, below, compound (3) may be prepared from commerically available aspartic and glutamic acid derivatives via oxazolidinones followed by reduction.

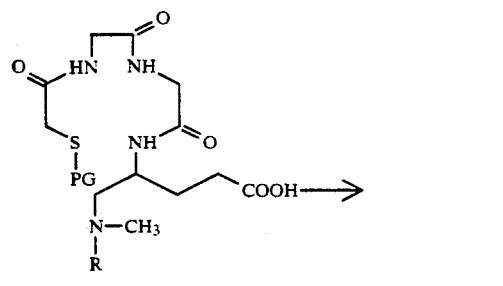

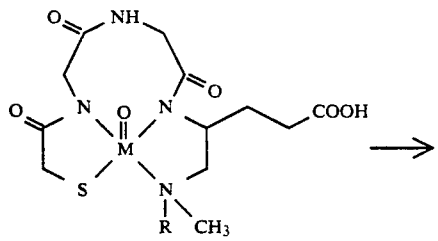

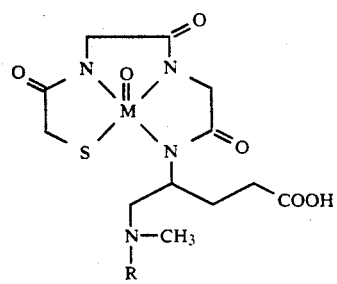

Since the amine-amide-thiolate intermediate complex acts as a built-in metal transfer agent, and since the intermediate complex forms under mild conditions, the overall formation kinetics of the amide-thiolate complex is improved.

The following examples are offered to further illustrate the synthesis of potential triamide-thiolate ligands within the scope of the present invention. These examples are intended to be purely exemplary and should not be viewed as a limitation on any claimed embodiment.

EXAMPLE 4

Synthesis of Triamide-Thiolate Ligand, Compound (1)

A modified amino acid, described above, is reacted according to chemical reactions well known to those skilled in the art to yield compound (1).

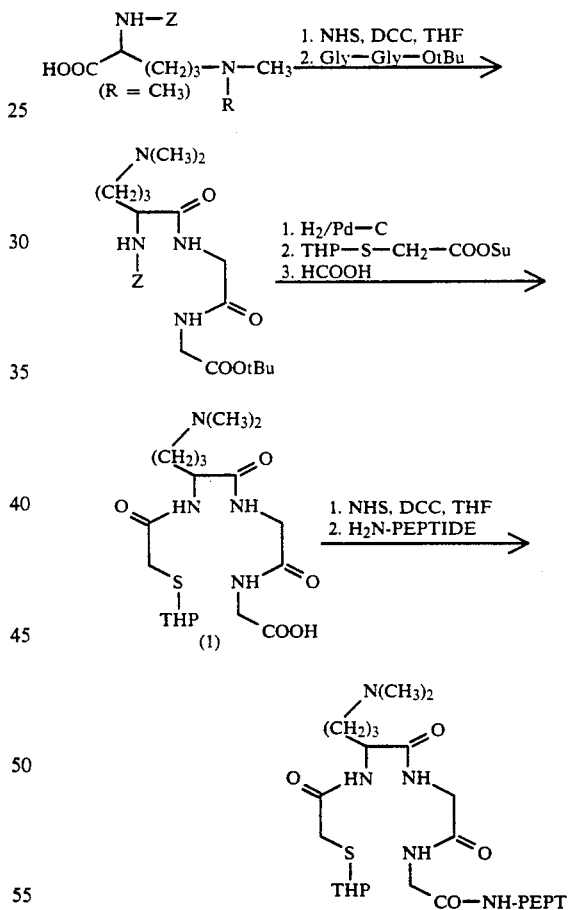

Where NHS is N-hydroxysuccinimide, Su is succinimide, and THP is 2-tetrahydropyranyl. As illustrated, the ligand may be coupled to a peptide according to techniques known in the art.

EXAMPLE 5

Synthesis of Triamide-Thiolate Ligand, Compound (2)

A modified amino acid, described above, is reacted according to chemical reactions well known to those skilled in the art to yield compound (2).

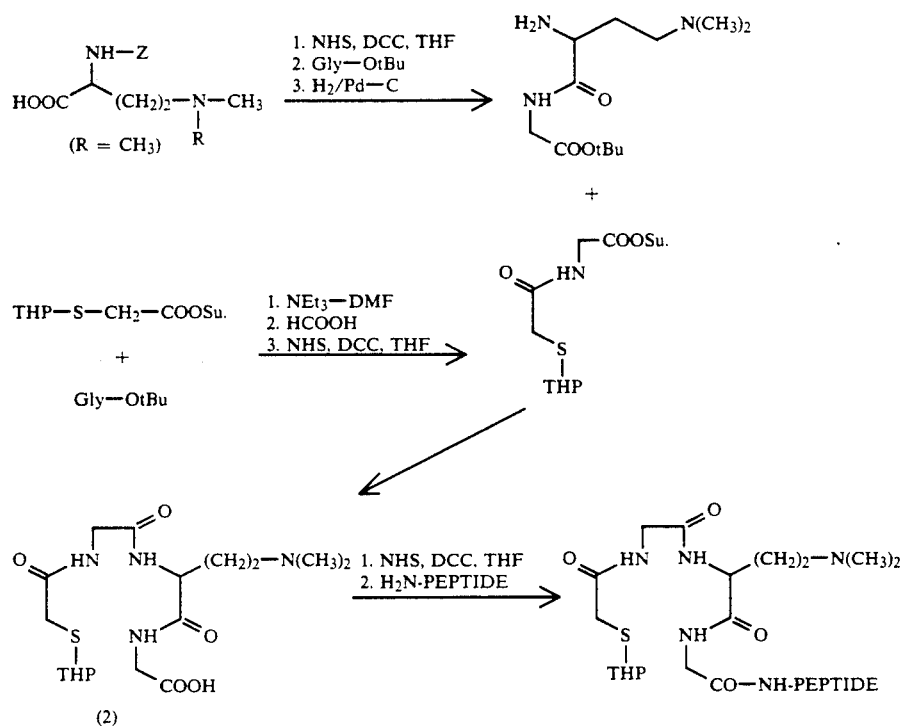

As illustrated, the ligand may be coupled to a peptide according to techniques known in the art.

EXAMPLE 6

Synthesis of Triamide-Thiolate Ligand, Compound (3)

A modified amino acid, described above, is reacted according to chemical reactions well known to those skilled in the art to yield compound (3).

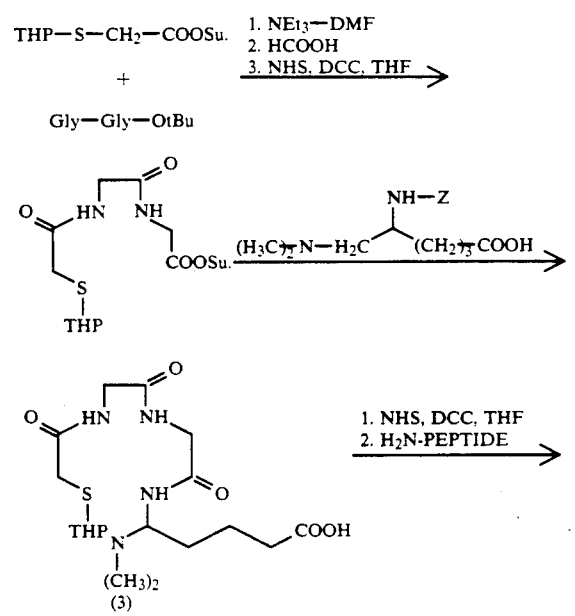

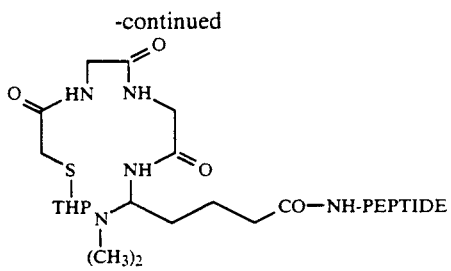

As described above, the ligands within the scope of the present invention may be coupled to biomolecules according to standard procedures known in the art. The conjugated biomolecules are then labeled with suitable radionuclides and administered to a patient for diagnostic imaging or therapeutic use.

After the amide-thiolate ligands of the present invention are prepared and labeled according to the procedure described above, the compounds may be used with a pharmaceutically acceptable carrier in conventional diagnostic imaging procedures. In this procedure, a diagnostically effective quantity of the compound, for example in the form of an injectable liquid, is administered to a warm-blooded animal and then imaged using a suitable detector, e.g. a gamma camera. Images are obtained by recording emitted radiation of tissue or the pathological process in which the radioactive peptide has been incorporated, which in the present care are tumors, thereby imaging at least a portion of the body of the warm-blooded animal.

Pharmaceutically acceptable carriers for either diagnostic or therapeutic use include those that are suitable for injection or administration such as aqueous buffer solutions, e.g. tris (hydroxymethyl)aminomethane (and its salts), phosphate, citrate, bicarbonate, etc., sterile water for injection, physiological saline, and balanced ionic solutions containing chloride and/or bicarbonate salts of normal blood plasma cations such as $Ca^{2+}$, $Na^+$, $K^+$ and $Mg^{2+}$. Other buffer solutions are described in *Remington's Practice of Pharmacy*, 11th edition, for example on page 170. The carriers may contain a chelating agent, e.g. a small amount of ethylenediaminetetraacetic acid, calcium disodium salt, or other pharmaceutically acceptable chelating agents.

The concentration of labeled biomolecule and the pharmaceutically acceptable carrier, for example in an aqueous medium, varies with the particular field of use. A sufficient amount is present in the pharmaceutically acceptable carrier in the present invention when satisfactory visualization of the tumor is achievable or therapeutic results are achievable.

From the foregoing, it will be appreciated that the present invention provides amide-thiolate ligands having improved complex formation kinetics which can be labeled under mild conditions and which have excellent complex stability.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A $N_3S$ ligand having the general structure:

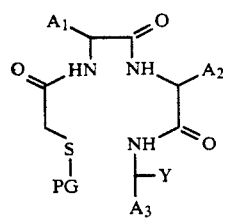

where at least $A_1$, $A_2$, or $A_3$ is $-(CH_2)_n NR_1R_2$, and at least one of the remaining $A_1$, $A_2$, or $A_3$ is $-(CH_2)_{n'}-X$, and the remaining $A_1$, $A_2$, or $A_3$ is H or an alkyl; Y is H or $-(CH_2)_{n''}-COOH$; X is a functional group for use in coupling the ligand to a biomolecule; $R_1$ and $R_2$ may be the same or different and are lower alkyl, $R_1$ or $R_2$ may optionally contain a functional group X, such that if $R_1$ or $R_2$ contains X, then the remaining $A_1$, $A_2$, or $A_3$ are H or an alkyl; n is from 2-5, n' is from 1-10, and n" is from 0-4; and PG is a sulfur protecting group.

2. A $N_3S$ ligand as defined in claim 1, wherein X is selected from the group consisting of a carbonyl, active ester, isocyanate, isothiocyanate, imidate, maleimide, halocarbonyl, halosulfonyl, and haloacetyl.

3. A $N_3S$ ligand as defined in claim 1, wherein PG is selected from the group consisting of ethoxyethyl, methoxymethyl, substituted and unsubstituted tetrahydrofuranyl and tetrahydropyranyl, acetamidoalkyl, S-alkanoyl, S-benzoyl, and S-substituted benzoyl groups.

4. A $N_2S_2$ ligand having the general structure:

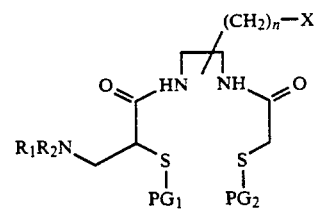

Where X is a functional group for use in coupling the ligand to a biomolecule; n is from 2-5; $R_1$ and $R_2$ may be the same or different lower alkyl group; and $PG_1$ and $PG_2$ may be the same or different and are sulfur protecting groups, at least $PG_1$ or $PG_2$ is acid labile.

5. A $N_2S_2$ ligand as defined in claim 4, wherein X is selected from the group consisting of a carbonyl, active ester, isocyanate, isothiocyanate, imidate, maleimide, halocarbonyl, halosulfonyl, and haloacetyl.

6. A $N_2S_2$ ligand as defined in claim 4, wherein at least $PG_1$ or $PG_2$ is selected from the group consisting of ethoxyethyl, methoxymethyl, substituted and unsubstituted tetrahydrofuranyl and tetrahydropyranyl, acetamidoalkyl, S-alkanoyl, S-benzoyl, and S-substituted benzoyl groups.

7. A diagnostic composition suitable for administration to a warm-blooded animal comprising:

a diagnostically effective quantity of a $N_3S$ ligand having the general structure:

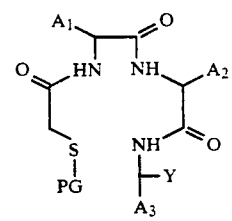

where at least $A_1$, $A_2$, or $A_3$ is $-(CH_2)_n NR_1R_2$, and at least one of the remaining $A_1$, $A_2$, or $A_3$ is $-(CH_2)_{n'}-X$, and the remaining $A_1$, $A_2$, or $A_3$ is H or an alkyl; Y is H or $-(CH_2)_{n''}-COOH$; X is a functional group for use in coupling the ligand to a biomolecule; $R_1$ and $R_2$ may be the same or different and are lower alkyl, $R_1$ or $R_2$ may optionally contain a functional group X, such that if $R_1$ or $R_2$ contains X, then the remaining $A_1$, $A_2$, or $A_3$ are H or an alkyl; n is from 2-5, n' is from 1-10, and n" is from 0-4; and PG is a sulfur protecting group, wherein the ligand in coupled to a biomolecule and wherein the ligand is complexed with a radionuclide selected from the group consisting of $^{99m}Tc$, $^{111}In$, and $^{62}Cu$; and a pharmaceutically acceptable carrier.

8. A therapeutic composition suitable for administration to a warm-blooded animal comprising:

a therapeutically effective quantity of a $N_3S$ ligand having the general structure:

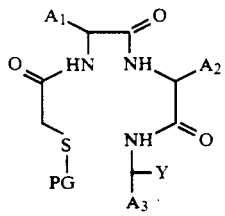

where at least $A_1$, $A_2$, or $A_3$ is $-(CH_2)_n NR_1R_2-$, and at least one of the remaining $A_1$, $A_2$, or $A_3$ is $-(CH_2)_{n'}-X$, and the remaining $A_1$, $A_2$, or $A_3$ is H or an alkyl; Y is H or $-(CH_2)_{n''}-COOH$; X is a functional group for use in coupling the ligand to a biomolecule; $R_1$ and $R_2$ may be the same or different and are lower alkyl, $R_1$ or $R_2$ may optionally contain a functional group X, such that if $R_1$ or $R_2$ contains X, then the remaining $A_1$, $A_2$, or $A_3$ are H or an alkyl; n is from 2-5, n' is from 1-10, and n'' is from 0-4; and PG is a sulfur protecting group, wherein the ligand in coupled to a biomolecule and wherein the ligand is complexed with a radionuclide selected from the group consisting of $^{186}$Re, $^{188}$Re, $^{67}$Cu, $^{90}$Y, and $^{60}$Co; and a pharmaceutically acceptable carrier.

* * * * *